United States Patent
Seidel et al.

(10) Patent No.: US 7,553,482 B2
(45) Date of Patent: Jun. 30, 2009

(54) USE OF A PHOSPHATE ADSORBENT TO COMBAT VASCULAR DISEASES

(75) Inventors: Dietrich Seidel, Feldafing (DE); Karl-Siegfried Boos, Gauting (DE)

(73) Assignee: Novartis International Pharmaceutical Ltd, Hamilton (BM)

( * ) Notice: Subject to any disclaimer, the term of this patent is extended or adjusted under 35 U.S.C. 154(b) by 397 days.

(21) Appl. No.: 10/480,476

(22) PCT Filed: Jun. 12, 2002

(86) PCT No.: PCT/EP02/06465

§ 371 (c)(1),
(2), (4) Date: Dec. 12, 2003

(87) PCT Pub. No.: WO02/100419

PCT Pub. Date: Dec. 19, 2002

(65) Prior Publication Data

US 2004/0186073 A1  Sep. 23, 2004

(30) Foreign Application Priority Data

Jun. 13, 2001 (DE) .............................. 101 28 511

(51) Int. Cl.
*A61K 31/70* (2006.01)
*A61K 31/715* (2006.01)
*A61K 31/717* (2006.01)
*A61K 31/721* (2006.01)
*A61K 31/722* (2006.01)
*A61K 33/26* (2006.01)
*A61P 19/00* (2006.01)
*A61P 19/08* (2006.01)
*A61P 9/00* (2006.01)
*A61P 9/10* (2006.01)

(52) U.S. Cl. ........................ 424/78.1; 424/400; 424/647; 514/23; 514/54; 514/57; 514/58; 514/59; 514/824; 514/866

(58) Field of Classification Search ................ 514/54, 514/23, 57, 58, 59; 424/78.1
See application file for complete search history.

(56) References Cited

U.S. PATENT DOCUMENTS 5,514,281 A * 5/1996 Boos et al. ................ 210/645

FOREIGN PATENT DOCUMENTS

DE 42 39 441 A 6/1994
WO WO 01 15720 A 3/2001

OTHER PUBLICATIONS

Webster's New World Dictionary, 2$^{nd}$ College ed., The World Publishing Co., NY, 1972, p. 1127, entry for "prevent."*
Medline Abstract, accession No. 2000099279 (2000).*
Medline abstract 96049545 (1996).*
Medline abstract 204233683 (2004).*
Medline abstract 1999313682 (1999).*
Medline abstract 2000361465 (2000).*
Medline abstract 2000285556 (2000).*
Medline abstract 2004173884 (2004).*
Medline abstract 1999446186 (1999).*
Medline abstract 2002053133 (2002).*
Block et al., "Association of serum phosphorus and calcium×phosphate product with mortality risk in chronic hemodialysis patients: a national study", American Journal of Kidney Diseases: The Official Journal of the National Kidney Foundation. United States Apr. 1998, vol. 31, No. 4, pp. 607-617.
Block et al., "Control of serum phosphorus: implications for coronary artery calcification and calcific uremic arteriolopathy (calciphylaxis)." Current Opinion in Nephrology and Hypertension. England Nov. 2001, vol. 10, No. 6, pp. 741-747.

* cited by examiner

*Primary Examiner*—John Pak
(74) *Attorney, Agent, or Firm*—Leslie Fischer

(57) ABSTRACT

The invention relates to the use of an adsorption material which has been modified with polynuclear metal oxide hydroxides for influencing the calcium level and, in particular, for treating or/and preventing atherosclerotic vascular diseases or/and disturbances of bone metabolism.

14 Claims, No Drawings

USE OF A PHOSPHATE ADSORBENT TO COMBAT VASCULAR DISEASES

This application is a 371 of PCT/EP02/06465, filed in Jun. 12, 2002.

The invention relates to the use of an adsorption material which has been modified with polynuclear metal oxide hydroxides for influencing the calcium level and, in particular, for treating or/and preventing atherosclerotic vascular diseases or/and disturbances of bone metabolism.

The invention also relates to a method of treating a patient suffering from atherosclerotic vascular disease and/or disturbance of bone metabolism, or lowering the risk of suffering from such disease or disturbance in a person with elevated risk of suffering from such disease or disturbance, said method comprising administering to said patient or person an adsorption material, which adsorption material is a mixture of an adsorption material modified with an iron III oxide hydroxide and an adsorption material modified with an iron III oxide hydroxide and pretreated with phosphate, in an amount effective to lower the concentration of phosphate and calcium in said patient's or person's blood.

The invention further relates to a method of treating a patient suffering from atherosclerotic vascular disease and/or disturbance of bone metabolism, or lowering the risk of suffering from such disease or disturbance in a person with elevated risk of suffering from such disease or disturbance, said method comprising administering to said patient or person an adsorption material modified with an iron III oxide hydroxide and pretreated with phosphate, in an amount effective to lower the concentration of calcium in said patient's or person's blood.

Clinical studies (e.g. G. A. Block et al., Am. J. Kidney Dis. 31 (1998), 607-617) performed on dialysis patients demonstrate that the relative risk of these patients dying increases as the calcium phosphate product in the serum increases, since elevated values of the calcium phosphate product promote calcification of the blood vessels, in particular the coronary vessels.

Lowering the calcium phosphate product could therefore increase the survival rate of dialysis patients, in particular.

Preference has previously been given to using per orally administrable phosphate binders, which are intended to prevent the phosphates present in the food in the gastrointestinal tract from being resorbed, as therapeutic agents for decreasing the phosphate concentration. Substances which are known to possess phosphate-binding properties are calcium salts (e.g.: calcium acetate, calcium carbonate, calcium citrate, calcium alginate, calcium gluconate, calcium lactate and calcium sulfate), magnesium carbonate and magnesium hydroxide and also aluminum hydroxide and aluminum carbonate.

Aside from these saliniform phosphate binders, DE 28 15 811 C2 (1978) has disclosed a macroporous sorption agent which is characterized in that it is an organic cation exchanger which is loaded with ions of at least one metal whose phosphate is only sparingly soluble.

Furthermore, Burt, H. M. et al. (J. Pharm. Sci. 75 (1978), 379-983) describes Dowex®-based anion exchangers which carry tertiary or quaternary amines as the functional group and adsorb inorganic phosphate in the intestinal tract.

However, these agents display substantial side effects in that the content of calcium in the patient serum is increased, which means that, despite a certain decrease in the phosphate concentration, only a relatively modest reduction in the calcium phosphate product is achieved.

German patent application 42 39 442.2 describes the use of an adsorption material which has been modified with polynuclear metal oxide hydroxides for selectively eliminating inorganic phosphate from protein-containing liquids, in particular body fluids. The agent is therefore outstandingly suitable for treating hyperphosphatemia. However, this document does not report any effect on calcium concentration.

It has been found, surprisingly, that, in contrast to previously employed phosphate binders, the adsorption material which has been modified with polynuclear metal oxide hydroxides decreases the calcium phosphate product significantly, e.g. by almost a third after a 28-day period of treatment.

The invention consequently relates to the use of an adsorption material which has been modified with polynuclear metal oxide hydroxides for treating or/and preventing atherosclerotic vascular diseases or/and disturbances of bone metabolism.

The invention also relates to the use of an adsorption material which has been modified with polynuclear metal oxide hydroxides for reducing the calcium phosphate product in the blood or serum.

In a preferred embodiment, the agent according to the invention is used in patients who are suffering from restricted renal function, in particular predialysis patients. Administration of the agent can in some cases result in a substantial prolongation of the predialytic stage. In another preferred embodiment, the agent is administered to dialysis patients.

Administering the agent reduces the phosphate concentration while at the same time maintaining or, in many cases, even reducing the calcium concentration. This thereby prevents calcification of the blood vessels, in particular the coronary vessels, of patients and consequently increases their survival rate.

The adsorption materials which have been modified with polynuclear metal oxide hydroxides are preferably employed in the form of pharmaceutical preparations which comprise the active compound in a form which is essentially not capable of being resorbed under physiological conditions. The preparation of such insoluble adsorption materials is described in detail in German patent application 42 39 442.2, the disclosure of which is hereby incorporated by reference. The preparation is particularly preferably effected by the unmodified adsorption material being brought into contact with a solution of an iron salt, e.g. iron(III) chloride, and then adjusting the pH to a value of >10, in particular >12, using a base, e.g. sodium hydroxide solution. The resulting precipitate is then washed, where appropriate after having been aged, and can, if necessary, be sterilized once again before use.

The adsorption materials are preferably selected from soluble or insoluble materials possessing organic or/and inorganic hydroxyl functionalities. Thus, it is possible, for example, to use organic supports, such as natural, semisynthetic or synthetic, linear or branched, soluble or insoluble carbohydrates, organic polymers or copolymers, e.g. agarose, dextran, dextrin, starch, amylose, amylopectin, cellulose or/and polyvinyl alcohol, as the basal material. On the other hand, it is also possible to use inorganic supports, in particular those based on silicon dioxide or/and silicate, such as glyceryl-modified glasses and glyceryl-modified silica gels. Carbohydrates, such as dextrans, are particularly preferred starting materials.

A large number of metals are suitable for being used as polynuclear metal oxide hydroxides, for example all transition metals, such as zirconium or else aluminum. However, iron is used as a particularly preferred metal since, with the metal possibly becoming detached to a lesser extent, iron is the metal which is to be regarded as that which is the least harmful for the body. For physiological reasons, therefore, trivalent iron is the metal which is most preferred even though other metals can also be used on account of their binding properties vis-à-vis the inorganic phosphate.

The adsorption materials which are used in accordance with the invention are distinguished by the fact that they do not to any significant extent release the polynuclear metal oxide hydroxide or metal ion, in particular the preferably employed iron(III) compound, which is bound covalently or coordinately to the support, even on contact with protein-containing liquids, such as whole blood and/or plasma, and consequently do not elicit any undesirable side effects, such as a disturbance of enteral iron resorption or of the cellular, and in particular the erythrocytic, iron metabolism in connection with the therapeutic extracorporeal or/and peroral use according to the invention.

The preparations can be administered in any suitable manner. In a preferred embodiment, the preparations are administered orally for enteral adsorption or elimination of inorganic phosphate or/and calcium. The oral preparations can be administered in the form of powders, tablets, capsules, etc., where appropriate coated with a gastric acid-resistant layer. On the other hand, the materials according to the invention can also be employed in an extracorporeal perfusion system for treating whole blood, plasma or/and dialysis liquid.

In a particularly preferred embodiment, it is possible to use an adsorption material which has already been pretreated with phosphate and which can be prepared by bringing the agent disclosed in German patent application 42 39 442.2 into contact with a phosphate-containing liquid, in particular an aqueous solution of phosphate. This phosphate-pretreated adsorber is particularly suitable for selectively decreasing the calcium content and is therefore preferentially employed, where appropriate together with a phosphate adsorber which has not been pretreated, for oral applications.

Since the agent is physiologically tolerated and to a large extent not resorbed, the daily treatment dose can essentially be selected at will. Thus, it is possible, for example, to administer, without difficulty, 2-20 g, or even more, of the preparation daily over a relatively long period.

The treatment is preferably a long-term treatment and has to be carried out for a period of at least 6 months if it is to display its optimal effect.

In addition, the invention will be explained by means of the following example. The polynuclear iron(III) oxide hydroxide-carbohydrate complex which is used in this example is the preparation which is prepared as described in Example 1 in German patent application 42 39 442.

EXAMPLE

The contents (mean values) of phosphate (2.1 mmol/l) and calcium (2.5 mmol/l) were first of all determined in the serum derived from 13 dialysis patients who were being treated with customary phosphate binders (calcium carbonate, calcium acetate, phosphonorm, Renagel®), and the calcium-phosphate product (5.25) was calculated from these mean values.

After that, the phosphate binders were discontinued for 7 days and the contents of phosphate (2.9 mmol/l) and calcium (2.2 mmol/l) were once again determined in serum and the calcium-phosphate product (6.38) calculated from these contents.

Treatment with the phosphate binder according to the invention (polynuclear Fe(III) oxide hydroxide-carbohydrate complex) then took place, initially at a daily dose of 4.6 g dry weight over a period of 14 days and then at a dose of 8.6 g for a further 14 days.

After a 28-day period of therapy, the content of phosphate was 1.8 mmol/l while that of calcium was 2.1 mmol/l. The calcium-phosphate product was calculated to be 3.78.

Result

Using the phosphate binder according to the invention surprisingly reduced the calcium-phosphate product by almost a third as compared with the phosphate binders which were previously employed.

The invention claimed is:

1. A method of treating a patient suffering from atherosclerotic vascular disease and/or disturbance of bone metabolism, or lowering the risk of suffering from such disease or disturbance in a person with elevated risk of suffering from such disease or disturbance, said method comprising:
  administering to said patient or person an adsorption material, which adsorption material is a mixture of an adsorption material modified with an iron III oxide hydroxide and an adsorption material modified with an iron III oxide hydroxide and pretreated with phosphate, in an amount effective to lower the concentration of phosphate and calcium in said patient's or person's blood.

2. The method of claim 1, wherein said adsorption material is a mixture of a carbohydrate modified with an iron III oxide hydroxide and a carbohydrate modified with an iron III oxide hydroxide and pretreated with phosphate.

3. The method of claim 1, wherein said patient or person is a predialysis patent suffering from restricted renal function.

4. The method of claim 3, wherein the administration of said adsorption material extends the predialytic stage.

5. The method of claim 1, wherein said adsorption material, which adsorption material is a mixture of an adsorption material modified with an iron III oxide hydroxide and an adsorption material modified with an iron III oxide hydroxide and pretreated with phosphate, is orally administered to said patient or person.

6. The method of claim 5, wherein said adsorption material is a mixture of a carbohydrate modified with an iron III oxide hydroxide and a carbohydrate modified with an iron III oxide hydroxide and pretreated with phosphate.

7. The method of claim 1, wherein said patient or person is a dialysis patient.

8. A method of treating a patient suffering from atherosclerotic vascular disease and/or disturbance of bone metabolism, or lowering the risk of suffering from such disease or disturbance in a person with elevated risk of suffering from such disease or disturbance, said method comprising:
  administering to said patient or person an adsorption material modified with an iron III oxide hydroxide and pretreated with phosphate, in an amount effective to lower the concentration of calcium in said patient's or person's blood.

9. The method of claim 8, wherein said adsorption material is a carbohydrate modified with an iron III oxide hydroxide and pretreated with phosphate.

10. The method of claim 8, wherein said patient or person is a predialysis patient suffering from restricted renal function.

11. The method of claim 10, wherein the administration of said adsorption material extends the predialytic stage.

12. The method of claim 8, wherein said adsorption material is orally administered to said patient or person.

13. The method of claim 12, wherein said adsorption material is a carbohydrate modified with an iron III oxide hydroxide and pretreated with phosphate.

14. The method of claim 8, wherein said patient or person is a dialysis patient.

* * * * *

UNITED STATES PATENT AND TRADEMARK OFFICE
CERTIFICATE OF CORRECTION

| | | |
|---|---|---|
| PATENT NO. | : 7,553,482 B2 | Page 1 of 1 |
| APPLICATION NO. | : 10/480476 | |
| DATED | : June 30, 2009 | |
| INVENTOR(S) | : Seidel et al. | |

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by 397 days.

Delete the phrase "by 397 days" and insert -- by 811 days --

Signed and Sealed this

Twentieth Day of April, 2010

David J. Kappos
*Director of the United States Patent and Trademark Office*